United States Patent
Easley et al.

(10) Patent No.: US 8,061,353 B2
(45) Date of Patent: Nov. 22, 2011

(54) METHOD AND APPARATUS FOR DELIVERING A DOSE OF A GASEOUS DRUG TO A PATIENT

(75) Inventors: Dan Easley, Apollo, PA (US); Aaron Dirks, Overland Park, KS (US); Robert McCoy, Apple Valley, MN (US)

(73) Assignee: Global Medical Holdings LLC, Adel, IA (US)

( * ) Notice: Subject to any disclaimer, the term of this patent is extended or adjusted under 35 U.S.C. 154(b) by 1061 days.

(21) Appl. No.: 11/684,370

(22) Filed: Mar. 9, 2007

(65) Prior Publication Data

US 2008/0216834 A1    Sep. 11, 2008

(51) Int. Cl.
*A61M 11/00* (2006.01)

(52) U.S. Cl. .......... 128/204.21; 128/204.26; 128/204.23

(58) Field of Classification Search .............. 128/204.21, 128/200.24, 203.12, 204.18, 204.23, 204.26, 128/201.21, 203.25, 205.11
See application file for complete search history.

(56) References Cited

U.S. PATENT DOCUMENTS

| | | | |
|---|---|---|---|
| 4,457,303 A * | 7/1984 | Durkan | 128/204.24 |
| 4,612,928 A * | 9/1986 | Tiep et al. | 128/204.23 |
| 4,686,975 A * | 8/1987 | Naimon et al. | 128/204.23 |
| 4,706,664 A * | 11/1987 | Snook et al. | 128/204.23 |
| 4,938,212 A | 7/1990 | Snook et al. | |
| 5,005,570 A | 4/1991 | Perkins | |
| 5,370,112 A | 12/1994 | Perkins | |
| 5,626,131 A * | 5/1997 | Chua et al. | 128/204.23 |
| 5,746,806 A | 5/1998 | Aylsworth et al. | |
| 5,890,490 A | 4/1999 | Aylsworth et al. | |
| 5,911,219 A | 6/1999 | Aylsworth et al. | |
| 5,938,118 A | 8/1999 | Cooper | |
| 6,220,244 B1 | 4/2001 | McLaughlin | |
| 6,532,958 B1 | 3/2003 | Buan et al. | |
| 6,880,556 B2 | 4/2005 | Uchiyama et al. | |
| 7,007,692 B2 | 3/2006 | Aylsworth et al. | |
| 7,066,180 B2 | 6/2006 | Aylsworth et al. | |
| 7,114,497 B2 | 10/2006 | Aylsworth et al. | |
| 7,153,271 B2 | 12/2006 | Aylsworth | |
| 7,213,594 B2 | 5/2007 | Aylsworth et al. | |
| 7,267,123 B2 | 9/2007 | Aylsworth et al. | |
| 2003/0140924 A1 | 7/2003 | Aylsworth et al. | |
| 2003/0145852 A1 | 8/2003 | Schmidt | |
| 2004/0159323 A1 | 8/2004 | Schmidt | |
| 2005/0121033 A1 * | 6/2005 | Starr et al. | 128/204.18 |
| 2006/0005842 A1 | 1/2006 | Rashad | |
| 2006/0011199 A1 | 1/2006 | Rashad | |
| 2006/0213519 A1 | 9/2006 | Schmidt | |
| 2006/0225737 A1 | 10/2006 | Iobbi | |
| 2006/0278223 A1 * | 12/2006 | Younes | 128/204.23 |

OTHER PUBLICATIONS

Limberg, Colvin, Correa, Costello, Morgan, Reis, "Changes in Supplemental Oxygen Prescription in Pulmonary Rehabilitation".

Somfay, Porszasz, Lee, Casaburi, "Dose-Response Effect of Oxygen on Hyperinflation and Exercise Endurance in Nonhypoxaemic COPD Patients", European Respiratory Journal, Jul. 2001, vol. 18 at 77-84.

(Continued)

*Primary Examiner* — Steven Douglas
(74) *Attorney, Agent, or Firm* — Beck & Thomas, P.C.

(57) ABSTRACT

A method and device that can vary the dose of a gaseous drug provided to a patient based on a comparison of the normal resting breath rate for each individual patient and the current breath rate of the patient so that the patient does not become desaturated.

19 Claims, 9 Drawing Sheets

OTHER PUBLICATIONS

Puente-Maestu, Garcia De Pedro, Marinez-Abad, Ruiz De Ona, Llorente, Cubillo, "Dyspnea, Ventilatory Pattern, and Changes in Dynamic Hyperinflation Related to the intensity of Constant Work Rate Exercise in COPD", Chest, Aug. 2005, vol. 128 at 651-656.

Diaz, Villafrance, Ghezzo, Borzone, Leiva, Milic-Emili, Lisboa, "Breathing Pattern and Gas Exchange at Peak Exercise in COPD Patients With and Without Tidal Flow Limitation at Rest", European Respiratory Journal, Jun. 2001, vol. 17 at 1120-1127.

Peters, Webb, O'Donnell, "Combined Physiological Effects of Bronchodilators and Hyperoxia on Exertional Dyspnea in Normoxic COPD", Thorax, Jul. 2006, vol. 61; 559-567.

"A Guide to Understanding Oxygen Conserving Devices 2003", Valley Inspired Products.

Written Opinion of the International Searching Authority for International Application No. PCT/US 08/55897; Reasoned statement under Rule 43bis.1(a)(i) with regard to novelty, inventive step, or industrial applicability; citations and explanations supporting such statement; Box No. V and Supplemental Box.

* cited by examiner

Table 1: Example Breath Rate Table

| | 80/20 Smoothing | | 90/10 Smoothing | |
|---|---|---|---|---|
| Current Breath Rate (BR$_{Cur}$) | Current Normal Breath Rate (BR$_{CurNorm}$) | New Normal Breath Rate (BR$_{NewNorm}$) | Current Normal Breath Rate (BR$_{CurNorm}$) | New Normal Breath Rate (BR$_{NewNorm}$) |
| Current Breath | Current Normal 80/20 | New Normal 80/20 | Current Normal 90/10 | New Normal 90/10 |
| 15.50 | 20.00 | 19.10 | 20.00 | 19.55 |
| 8.90 | 19.10 | 17.06 | 19.55 | 18.49 |
| 8.90 | 17.06 | 15.43 | 18.49 | 17.53 |
| 8.90 | 15.43 | 14.12 | 17.53 | 16.66 |
| 12.90 | 14.12 | 13.88 | 16.66 | 16.29 |
| 12.90 | 13.88 | 13.68 | 16.29 | 15.95 |
| 15.00 | 13.68 | 13.95 | 15.95 | 15.85 |
| 15.00 | 13.95 | 14.16 | 15.85 | 15.77 |
| 15.00 | 14.16 | 14.33 | 15.77 | 15.69 |
| 14.40 | 14.33 | 14.34 | 15.69 | 15.56 |
| 14.40 | 14.34 | 14.35 | 15.56 | 15.45 |
| 13.90 | 14.35 | 14.26 | 15.45 | 15.29 |
| 13.90 | 14.26 | 14.19 | 15.29 | 15.15 |
| 13.90 | 14.19 | 14.13 | 15.15 | 15.03 |
| 13.20 | 14.13 | 13.95 | 15.03 | 14.84 |
| 13.20 | 13.95 | 13.80 | 14.84 | 14.68 |
| 12.10 | 13.80 | 13.46 | 14.68 | 14.42 |
| 12.10 | 13.46 | 13.19 | 14.42 | 14.19 |
| 12.10 | 13.19 | 12.97 | 14.19 | 13.98 |
| 14.30 | 12.97 | 13.23 | 13.98 | 14.01 |
| 14.30 | 13.23 | 13.45 | 14.01 | 14.04 |
| 14.00 | 13.45 | 13.56 | 14.04 | 14.04 |
| 14.00 | 13.56 | 13.65 | 14.04 | 14.03 |
| 15.80 | 13.65 | 14.08 | 14.03 | 14.21 |
| 15.80 | 14.08 | 14.42 | 14.21 | 14.37 |
| 15.80 | 14.42 | 14.70 | 14.37 | 14.51 |

Fig. 4

Chart 1:

METHOD AND APPARATUS FOR DELIVERING A DOSE OF A GASEOUS DRUG TO A PATIENT

BACKGROUND OF THE INVENTION

1. Field of the Invention

This invention generally relates to a method of delivering doses of a gaseous drug through an ambulatory device to treat a patient with lung disease. The invention more particularly relates to an ambulatory device that provides a specific dose of a gaseous drug to a patient on each breath and can vary that dose to adjust to the patient's needs, as well as deliver it at various flow rates to maximize comfort and decrease noise.

2. Description of Related Art

The treatment of patients with lung disease often involves the use of ambulatory oxygen dosing systems.

Oxygen dosing systems are currently commonly referred to as conserving devices because they only allow oxygen to be provided at fixed flows during a specific portion of the inhalation cycle. Conservers typically get oxygen from high pressure tanks that are delivered to the patient by an oxygen dealer. The design of these units is to conserve oxygen so that oxygen is not provided when the patient cannot use it and therefore it is not wasted. These types of devices were focused on using less oxygen so that deliveries of the tanks to the patient were less frequent and thereby saving costs. However, while these conservers are often effective at using less oxygen, they do not dose the patient properly. Clinical information on these types of devices can be found in, "A Guide to Understanding Oxygen Conserving Devices 2003" by Valley Inspired Products which is herein incorporated by reference.

Research on oxygen conserving devices dosing can be found in the following documents which are herein incorporated by reference: (a) Trina M. Limberg, Roberta S. Colvin, Maria Correa, Rosanna Costello, Cindy G. Morgan, and Andrew L. Reis, "*Changes in Supplemental Oxygen Prescription in Pulmonary Rehabilitation*"; (b) A. Somfay, J. Porszasz, S. M. Lee, and R. Casaburi, "*Dose-Response Effect of Oxygen on Hyperinflation and Exercise Endurance in Non-hypoxaemic COPD Patients*", European Respiratory Journal, July 2001, volume 18 at 77-84; (c) Luis Puente-Maestu, Julia Garcia de Pedro, Yolanda Marinez-Abad, Jose Maria Ruiz de Ona, Daniel Llorente, and Jose Manuel Cubillo, "*Dyspnea, Ventilatory Pattern and Changes in Dynamic Hyperinflation Related to the Intensity of Constant Work Rate Exercise in COPD*", Chest, August 2005, volume 128 at 651-656; (d) O. Diaz, C. Villafranca, H. Ghezzo, G. Borzone, A. Leiva, J. Milic-Emili, and C. Lisboa, "*Breathing Pattern and Gas Exchange at Peak Exercise in COPD Patients With and Without Tidal Flow Limitation at Rest*", European Respiratory Journal, June 2001, volume 17 at 1120-1127; and (e) Peters, MM, Webb, K A, and O'donnell, De, "*Combined Physiological Effects of Bronchodilators and Hyperoxia on Exertional Dyspnea in Normoxic COPD*", Thorax, July 2006, volume 61 at 559-567.

The fixed flow conserver devices can be categorized into either constant minute volume or constant volume conservers.

Constant volume devices really are fixed flow/variable time. On a device that has patient settings of 1-6, which can correspond to a patient's LPM prescription, each setting would provide a fixed volume per breath delivered. An example of this type of device can be seen in U.S. Pat. Nos. 5,005,570 and 5,370,112 to Perkins. These types of devices in commercial application typically have different settings to provide different volumes of oxygen. These devices typically provide for 16 cc of volume for each setting, so that a patient who is on a 2 setting would receive 32 cc of oxygen at each inhalation cycle. The flow is fixed by an orifice against a known pressure and the device calculates the valve on-time to deliver a desired volume. This flow and valve on-time is the same for a patient who is breathing at 12 breaths per minute ("BPM") as it is for a patient who is breathing at 35 BPM. The device is designed to handle the highest expected breath rate and therefore, delivers a higher than necessary flow in a shorter than necessary window for patients breathing at a more relaxed rate.

Constant minute volume devices simply act as on/off valves at a fixed flow and do not predetermine a dose, but rather are demand valves. They turn on during inhalation, and turn off during exhalation. These devices simply supply the patients' prescription flow. Since the I:E ratio is thought to remain constant, 1:2 for example, it is thought that the valve will be on for a fixed percentage of the time in the course of a minute, and therefore are called constant minute devices. Constant minute volumes also often insert an accumulator chamber that is replenished during valve off times. Assuming that the device fills this accumulator at a fixed rate (often 0.7-1 SLPM), then the patient depletes this on every breath. The patient can never get more than the limit of 1 SLPM of oxygen and if they breathe too fast, the accumulator can not be filled due to recovery time.

The above non-feedback devices do not adjust for a larger dose per breath as the patient ambulates, and in many cases, the patients will desaturate, i.e. have low oxygen levels in bloodstream.

Also, because the non-adjusting units give fixed doses at fixed flows, they do not adjust the flow down to minimize the flow required for that breath dose of oxygen. Fixed volume units give a specific, repeated dose by opening the valve for a fixed time, regardless of the inhalation time. Because the flow is not minimized there is noise created through the nasal canula, creating an unpleasant experience for the oxygen patient because the flow can startle the patient and cause nasal dryness.

The above prior art devices also are inefficient because oxygen is wasted. Oxygen from the above devices can be delivered during the second half of inhalation. Oxygen delivered during the second half of inhalation fills the upper airway where no gas exchange takes place and has no therapeutic value. Additionally the above devices do not deliver doses that fit the patient's need when their breath rate rises.

Further, some clinical personnel have migrated to using two prescriptions for a patient; one for rest and another, higher setting for the patient to use during ambulation. This points out the need for additional oxygen during exercise, but also puts the burden on the patient to remember to turn up their conserver when they get up and start walking, and then to remember to turn it back down when they sit down. Many of these patients are in their later years and can often forget to turn the device up or down, resulting in desaturation, or oxygen being wasted respectively.

Other than the above devices there are devices that use pulse oximetry as a feedback method and then adjusts to provide a target oxygen saturation. Examples of such devices can be found in U.S. Pat. No. 6,532,958 to Buan et al.; U.S. Patent Application Publication No. 20060225737 to Iobbi; U.S. Patent Application Publication No. 20060213519 to Schmidt; U.S. Patent Application Publication No. 20060011199 to Abdul-Aziz; U.S. Patent Application Publication No. 20060005842 to Abdul-Aziz; U.S. Patent Application Publication No. 20040159323 to Schmidt; and U.S. Patent Application Publication No. 20030145852 to Schmidt.

However, oximetry is a very cumbersome means of feedback. A separate oximetry sensor must be attached to the patient usually on the patient's finger. Additionally, oximetry is not very accurate on a patient who is ambulatory.

U.S. Pat. No. 6,880,556 tries to address the deficiencies with the prior art conservers. To do this U.S. Pat. No. 6,880,556 uses a predetermined normal breath rate. This breath rate is used for all patients. A person of ordinary skill in the art would believe that there is a universal breath rate that could be used, such as 20 bpm, that is the normal resting breath rate for all people and that this could be used to effectively dose all patients. U.S. Pat. No. 6,880,556 uses an on/off valve to deliver a volume of oxygen. All of the oxygen is delivered at the same flow rate.

Historically, everybody skilled in the art and in the industry assume that the normal resting breath rate is 20 breaths per minute. One of ordinary skill in the art would expect to be able to use 20 breaths per minute; and that at 20 breaths per minute, all patients would be kept saturated.

However, through extensive research and clinical work we have figured out that there is not a normal resting breath rate that applies to all people. We have discovered that normal resting breath rate is not the same for every patient. There is a normal resting breath rate for each and every patient that is particular to that patient and the normal resting breath rate for each individual patient varies over time. It can even vary through the day. The normal resting breath rate for a person can vary from hour to hour.

BRIEF SUMMARY OF INVENTION

The object of this invention is to overcome the deficiencies of the prior art.

Another object of this invention is to deliver oxygen to patients so that all patients remain saturated at all times.

This invention provides for a method of giving a patient that has a respiratory disorder and has breathing function a dose of a gaseous drug. A normal resting breath rate for the patient is determined. The current breath rate for the patient is monitored. The current breath rate is compared with the normal resting breath rate. Based on the comparison a dose is provided to the patient. The dose can be delivered during the first two-thirds of an inhalation cycle. Normal resting breath rate is determined by a control circuit. Changes in the inhalation to exhalation ratio can also be considered when providing the dose. This invention also provides for a method of giving a patient that has a respiratory disorder and has breathing function a dose of a gaseous drug using the ratio of inhalation to exhalation.

This invention also provides for a method of giving a patient that has a respiratory disorder and has breathing function a dose of a gaseous drug using an inhalation window.

This invention also provides for an apparatus for giving a patient that has a respiratory disorder and has breathing function a dose of a gaseous drug. The apparatus has a control circuit connected to a vacuum pressure sensor that is connected to a patient to sense patient inhalation information. The control port has a connection port for connection to a gaseous drug supply. The apparatus has a gaseous drug delivery device that allows the volume and flow of the gaseous drug to be varied. The gaseous drug delivery device could be a low flow valve and a high flow valve. Alternatively, the gaseous drug delivery device could be a variable flow valve.

BRIEF DESCRIPTION OF THE DRAWING

FIG. 4 is an Example of a Breath Rate Table.

DETAILED DESCRIPTION OF THE INVENTION

Definitions

Figure 1:
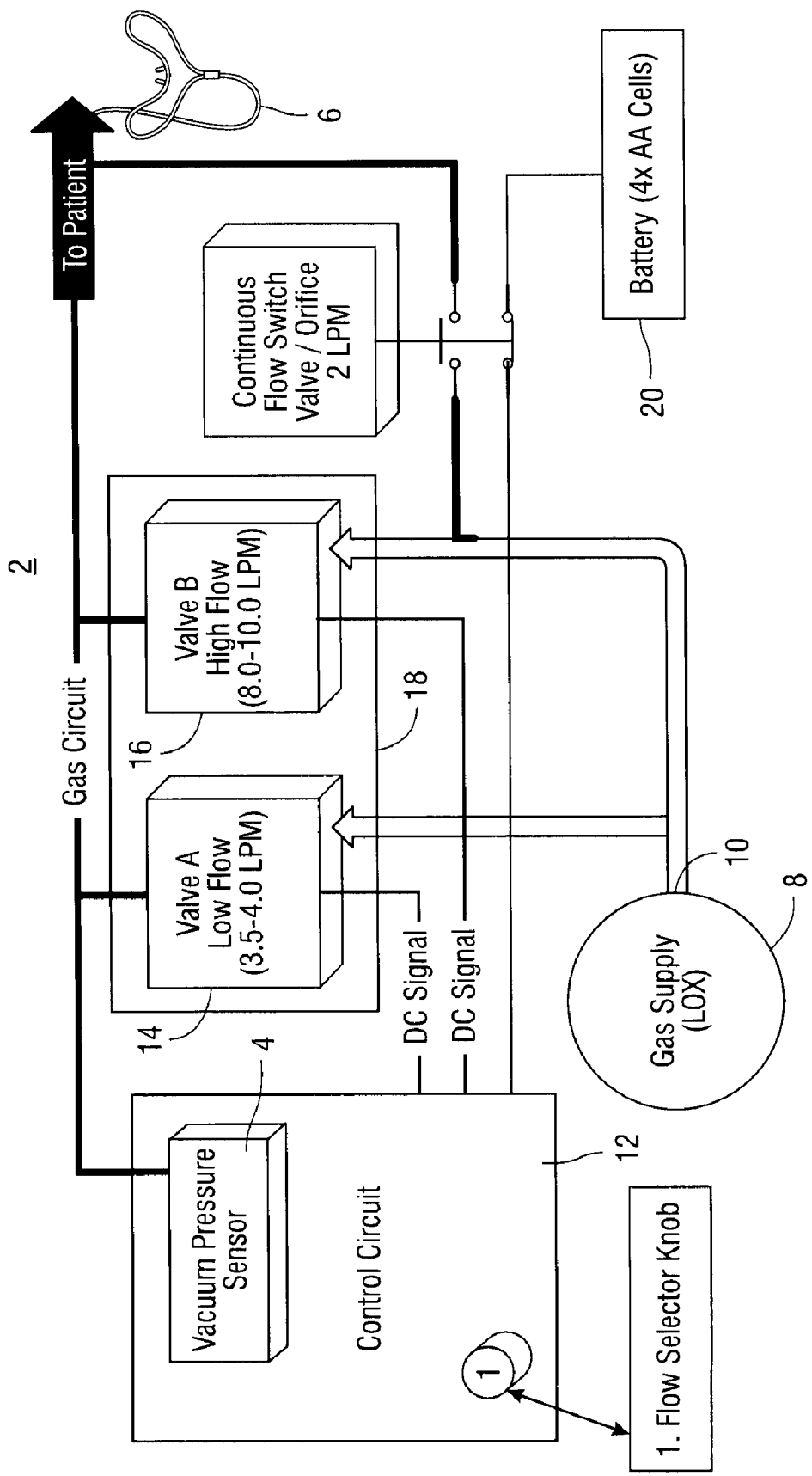
FIG. 1 is a block diagram of the apparatus for providing a dose of a gaseous drug.

Breath rate—the amount of breaths taken in a period of time. Typically this would be breaths per minute.

Normal resting breath rate—The usual amount of breaths for a patient under normal resting conditions. Normal breath rate varies for each person and can vary from day to day and hour to hour. Normal resting breath rate needs to be monitored and can be smoothed.

Determining a normal resting breath rate for the patient at a particular time—Finding the normal resting breath rate for an individual patient at a certain time. This is a measured value calculated using an algorithm for an individual patient. The normal resting breath rate for the patient at a particular time can be a smoothed averaged baseline. It can be determined by taking the Current Breath Rate ($BR_{Cur}$), and the Current Normal Breath Rate ($BR_{CurNorm}$), and weighting them both proportionately, 20%, and 80% respectively or 10%, and 90% respectively, (or some similar ratio), to establish the New Normal Breath Rate ($BR_{NewNorm}$). This calculation is made on every breath except when the patient is not at rest. When the device is first connected the first current Breath rate is 20. The rate is calculated continuously. However, if the current breath rate exceeds the current Normal Breath rate by a value from +2 to +5 then the current breath rate is not used in the calculation of the normal resting breathe rate because an increase of such shows that the patient is not at rest. Preferably the value that is used is +3. So for example if the $BR_{CurNorm}$ is 12 and the $BR_{Cur}$ is 16 this value is not used in the calculation of $BR_{NewNorm}$, It is also desirable to allow a settling time after non-rest periods such that a 2 minute delay is imposed after a patient's breath rate climbs. Using the previous example, when the patient with a $BR_{CurNorm}$ of 12 is ambulating and their breath rate climbs to 16, they are viewed as "not at rest". When they stop exercising, their breath rate declines, but there is a settling time required for the patient to stabilize. As such, the unit excludes breaths when a patient exceeds $BR_{CurNorm}$ by +3 and then continues to exclude breaths for 2 minutes after they drop back below the +3 threshold.

Providing a dose—Supplying a volume of gas. This could be fixed volume, a predetermined defined pulse or fixed minute volume or any other method of supplying a volume of gas. The volume could be varied based on the breath rate.

Gaseous drug—a gas recognized in the official United States Pharmacopeia. Examples are Oxygen, Nitrous Oxide, and Nitrogen.

Providing a dose of a gaseous drug—supplying a volume of a drug in gas form such as oxygen to a patient. The dose is less than the patient's tidal volume which is the amount of air breathed in or out during normal respiration.

Chronic Obstructive Pulmonary Disease ("COPD")—is a lung disease that makes it difficult for a person to breathe. The airways for a person to be able to inhale and exhale are blocked. When COPD is severe, it can prohibit patients from doing basic tasks, such as walking a distance. COPD is also sometimes called Emphysema or chronic bronchitis. Oxygen therapy is used to treat COPD. Patients with COPD could be treated with the method and apparatus described.

Respiratory disorder—an illness involving respiratory function that can be treated. They would include COPD, interstitial pulmonary fibrosis and other illnesses that require oxygen therapy. It would not include a situation where oxygen is being used for life support.

Breathing function—A person is able to breathe on their own without life support.

Monitoring the current breath rate—observing the breath rate at a point and time.

Comparing the current breath rate with the normal resting breath rate—taking the current breath rate and evaluating it with respect to the normal resting breath rate. For example the normal resting breath rate could be 15 and the current breath rate could be 30 indicating a need for additional oxygen.

Providing a dose of the gaseous drug based on the comparison of the current breath rate with the normal breath rate—delivering a dose based on the difference between the current breath rate and the normal resting breath rate. For example if the normal resting breath rate was 12 and the current breath rate was 16 a dose of 32 cc might be delivered instead of 16 cc.

Typically the patient will have different settings that can be used with each setting delivering an additional 16 cc per setting. When the comparison shows a +3, +4 or +5 increase in breath rate and additional 16 cc dose is given. This would be considered sport mode. A second additional 16 cc is given if the patient goes over a second threshold of +6, +7, or +8.

Dose is delivered during a first two-thirds of an inhalation cycle—providing a volume of gas to a patient within the first two-thirds of time when the patient is breathing in.

Determining a standard ratio of inhalation time to exhalation time during a breath for a patient—A breath occurs when a patient breathes in and then exhales. It takes a person a certain amount of time to breathe in and then exhale. "A ratio of inhalation time to exhalation time during a breath for a patient," would be a comparison of the time it takes a patient to breathe in versus the time it takes a person to exhale. An average ratio would be 1:2. 1 second inhale and 2 second exhale would give a 3 second breath cycle and a breath rate of 20 breaths per minute. This ratio could be a predetermined fixed value or it could be a value determined for an individual patient.

Monitoring the ratio of inhalation time to exhalation time—observing the ratio of inhalation time to exhalation time for a patient.

Adjusting the dose of the gaseous drug provided based on a change in the ratio of inhalation and exhalation—A volume of the gas has already been determined based on the breath rate however, that volume may be varied after considering the change in the ratio of inhalation to exhalation.

Predetermining a fixed value—deciding in advance a set quantity to be used.

A control circuit—A programmable controller that could be a small computer used for automation of processes, such as control of machinery. The control usually uses a microprocessor. The program is usually created by a skilled technician. The program is stored in memory. There are special input/output arrangements. These connect the control to a process' sensors and actuators. The control circuit reads information being monitored on the patient and then drives hydraulic cylinders or diaphragms, magnetic relays or solenoids to control the dose being delivered.

Connected to—coupled with

Vacuum sensor—a device that determines changes in a gas stream. This could also be a pressure sensor and is included in the definition of vacuum sensor.

Senses a patient's inhalation—determining when a person inhales. The same canula tube is used to sense inhalation as is used to deliver oxygen, so that the sensor is ignored during the gas delivery time. The sensor communicates that inhalation has begun, and the processor delivers the dose, at which time the vacuum sensor is ignored. When the dose is finished, the vacuum sensor is again monitored and the end of inhalation and start of exhalation transition can be noted.

Breath rate monitored by the vacuum sensor and provided to the control circuit—the vacuum sensor looks at the breath rate and gives the information to the control circuit.

Normal resting breath rate is compared with current breath rate by the control circuit—the control circuit determines whether the current breath rate is higher, lower, or the same as the normal resting breath rate.

Control circuit determines the dose of the gaseous drug to fit the need of the patient—based on the comparison of the current breath rate with the normal resting breath rate, the control circuit selects an amount of the gaseous drug to be provided to the patient.

Control circuit adjusting a valve to deliver an appropriate dose and flow to the patient—the control circuit can have a valve closed or opened so that the patient receives the correct volume of gaseous drug and either controls the flow by choosing different valves or through a proportional valve.

Control circuit choosing from a low flow valve, a high flow valve, a combination of the low flow and high flow valve or a continuous flow switch to deliver an appropriate dose to the patient—after determining the appropriate flow required so that the oxygen is delivered to patient within the first ⅔ of the inhalation window the control circuit can select a valve or combination of valves.

Comparing the current ratio of inhalation time to exhalation time with the standard ratio of inhalation time to exhalation time—taking the current ratio of inhalation time to exhalation time and evaluating it with respect to the standard ratio of inhalation time to exhalation time.

Providing a dose of gas based on the comparison of the current ratio of inhalation time to exhalation time with the standard ratio of inhalation time to exhalation time—supplying a volume of a drug in gas form such as oxygen to a patient. The volume can be varied based on the comparison of the current inhalation time to exhalation time with the standard ratio of inhalation time to exhalation time.

Senses a patient's inhalation time and exhalation time—determining the time it takes for a patient to inhale and the time it takes for a patient to exhale.

Current ratio of inhalation time to exhalation time is monitored by the vacuum sensor and provided to the control circuit—the vacuum sensor takes the current ratio of inhalation time to exhalation time and relays the information to the control circuit.

Determining an inhalation window—figuring out the time it takes for inhalation. This could be a predetermined amount of time or actually figured out based on a particular patient. The current breath rate at the last breath, is used to determine the delivery window for the next breath.

Determining an amount of the dose of the gaseous drug based on a duration of the inhalation window—basing a volume of the gaseous drug on the time of the inhalation window.

Delivering the dose of the gaseous drug within a second inhalation window—providing a volume of the gaseous drug to the patient while the patient is inhaling.

Dose is delivered during a first two-thirds of the second inhalation cycle—providing a volume of gas to a patient within the first two-thirds of time when the patient is breathing in after the inhalation cycle is determined. For example if the inhalation cycle is a predetermined value then the second inhalation cycle would be the first inhalation by the patient. If the inhalation cycle is first determined as the patient takes the first breath with the apparatus connected then the second inhalation would be the when the volume of gaseous drug is delivered.

Transmits the patient inhalation information to the control circuit—sending information regarding inhalation to the control circuit.

Connection port—place to link the gaseous drug with the apparatus.

Connection to a gaseous drug supply—Any type of gaseous drug storage container or supply device.

Gaseous drug delivery device—a device that controls the volume and flow of the gaseous drug that is provided to the patient.

Allows the volume of the gaseous drug delivered to the patient to be varied—the amount of the gaseous drug delivered can be changed.

Power supply—something that provides electricity. It could be batteries.

Low flow valve—a valve that permits between 3.5-4.0 liters per minute. An example of this type of valve is one made by Parker Hannifin's Pneutronics Division. Parker Hannnifin introduced a two-position, three-way, digital valve that is only 8 mm wide. The new modular device, called the X-valve, is made of glass reinforced PBT (polybutylene terephthalate) and may be customized to meet a wide variety of medical and analytical applications.

The modular design lets several valves mount side-by-side in a compact manifold arrangement. The assembly is smaller than conventional systems, but the size does not compromise its operation. X-valves have a response time less than 10 msec and weigh about half that of valves in similar applications. Moreover, the valve uses fewer parts, which means less tolerance problems and fewer potential leak points with improved reliability. This valve is used with an orifice that will allow the flow to be 3.5-4.0 liters per minute. Parker Pneutronics' X valves, or Parker Pneutronics' V2 Series valves, or Festo 10 mm MHP-1 solenoid valves can be used.

Controlled by the control circuit—the control circuit operates.

High flow valve—valve that permits between 8.0-10 liters per minute. An example of this type of valve is the same Parker Hannnifin X-valve, however, a different orifice is used so that the flow is between 8.0-10 liters per minute.

Continuous flow valve—is a valve that allows 2 liters per minute of flow. Can be any fixed liter flow based on the orifice or CV of the valve/orifice combination, and the pressure at the input. In one embodiment a 22-25 psig pressure regulation is used at the gas input.

Variable flow valve—a valve that can allow for different flow rates. An example of this type of valve is Festo proportional valve with MHP-1 valve body.

Oxygen Conserver: a device that limits flow of oxygen to effective portions of the breath cycle. They vary from a simple demand valve that is on during inhalation and off during exhalation, to a fixed dose pulse of oxygen delivered at the front end of the inhalation cycle.

Oxygen Saturation—oxygen saturation ($SaO_2$) measures the percentage of hemoglobin binding sites in the bloodstream occupied by oxygen. At low partial pressures of oxygen, most hemoglobin is deoxygenated. At around 90% (the value varies according to the clinical context) oxygen saturation increases according to an S curve and approaches 100% at partial oxygen pressures of >10 kPa. A pulse oximeter relies on the light absorption characteristics of saturated hemoglobin to give an indication of oxygen saturation.

Desaturation, or Hypoxemia—An $SaO_2$ (arterial oxygen saturation) value below 90% is termed hypoxemia.

Sport mode—occurs when an extra dose of oxygen is provided because the patient's breath rate increases. Typically, if the current breath rate is +3 then sport mode is entered and an extra dose is delivered.

DESCRIPTION

FIG. 1 shows a dosing apparatus 2 for providing a dose of gaseous drug. The dosing apparatus 2 is connected to a patient through a cannula tube 6 and to a gaseous drug supply 8 through a connection port 10. The dosing apparatus 2 has a vacuum pressure sensor 4, (it can be a vacuum or pressure sensor; and hereinafter will be referred to as a "vacuum sensor") which monitors ongoing inhalation and exhalation. The information obtained by the vacuum sensor 4 is sent to the control circuit 12 where it determines a normal resting breath rate, an inhalation window, a standard inhalation to exhalation ratio, the current inhalation to exhalation ratio and current breath rate for the patient.

Once all of the information is gathered the control circuit 12 then uses an algorithm to calculate and determine the amount of the dose, the estimated delivery time window for the next dose, and the minimum flow rate that can be used to deliver the dose within the delivery window, based on a comparison of the normal resting breath rate with the current breath rate. At that point the control circuit selects from a low flow valve 14, a high flow valve 16, or a combination of both valves 14 & 16 to deliver the appropriate dose to the patient. A gaseous drug delivery device 18 in the embodiment is the combination of low flow valve 14 and high flow valve 16.

Typically the gaseous drug is oxygen. The dosing apparatus 2 may be powered by a battery 20.

Typically the control circuit 12 would use the normal resting breath rate and compare it with the standard breath rate to calculate the dose of oxygen required for the patient. Alternatively the standard inhalation to exhalation ratio could be compared to the current inhalation to exhalation ratio to calculate the dose of the oxygen. An additional alternative could be that an inhalation window is selected and a dose calculated based on the duration of the window.

In an alternative embodiment of the invention, an inhalation window or a standard inhalation to exhalation ratio could be preprogrammed with set values for the standard inhalation window or a standard inhalation to exhalation ratio instead of the control circuit calculating this value.

Figure 9:
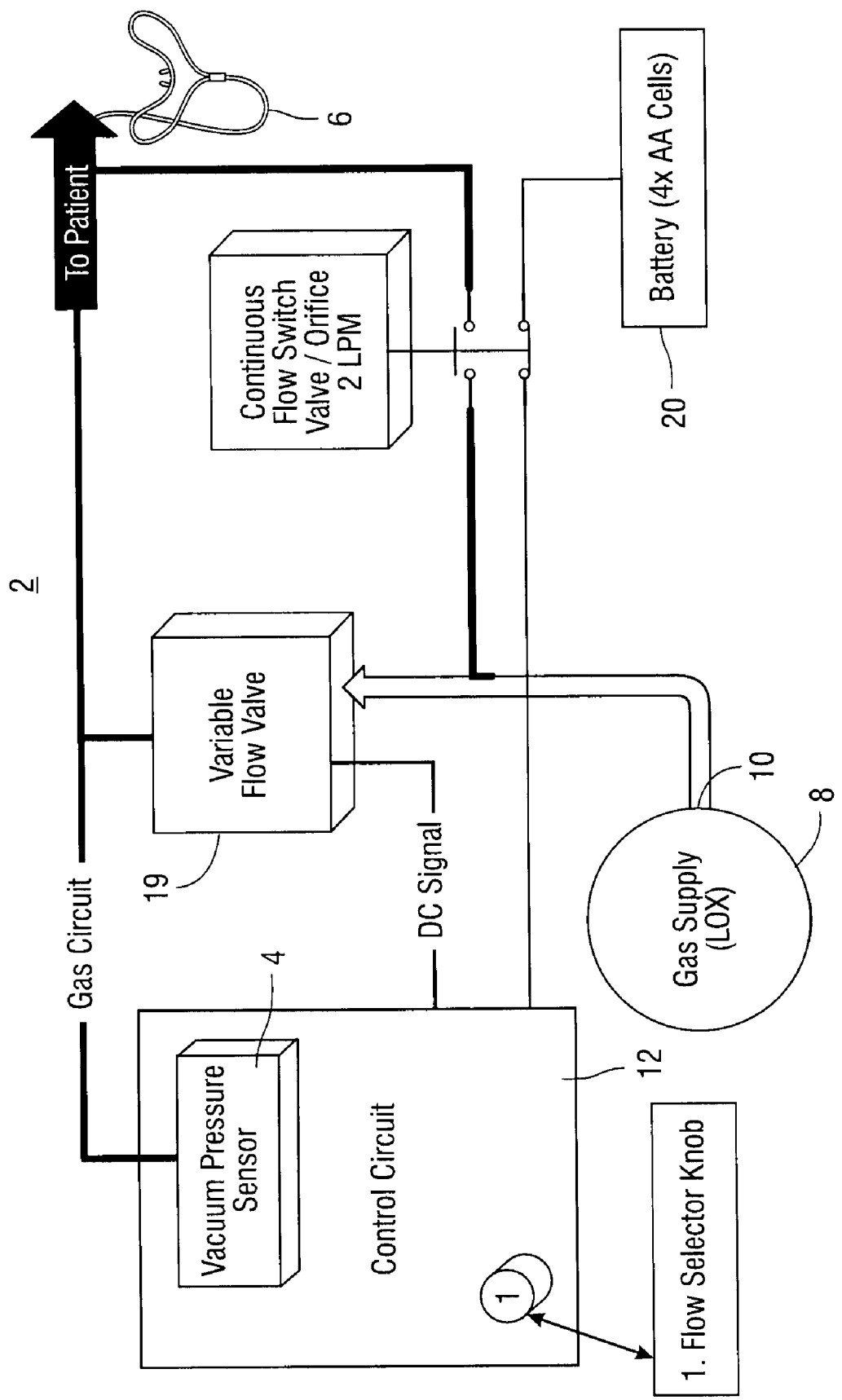
FIG. 9 is a block diagram of the apparatus for providing a dose of a gaseous drug with a variable flow valve.

As another alternative embodiment we could incorporate a single variable flow valve 19, as shown in FIG. 9, instead of multiple valves which would allow for a greater number of choices for flow and would fit the dose to the window more closely across the range of possibilities. The single variable flow valve 19 is the gaseous drug delivery device.

Figure 3:
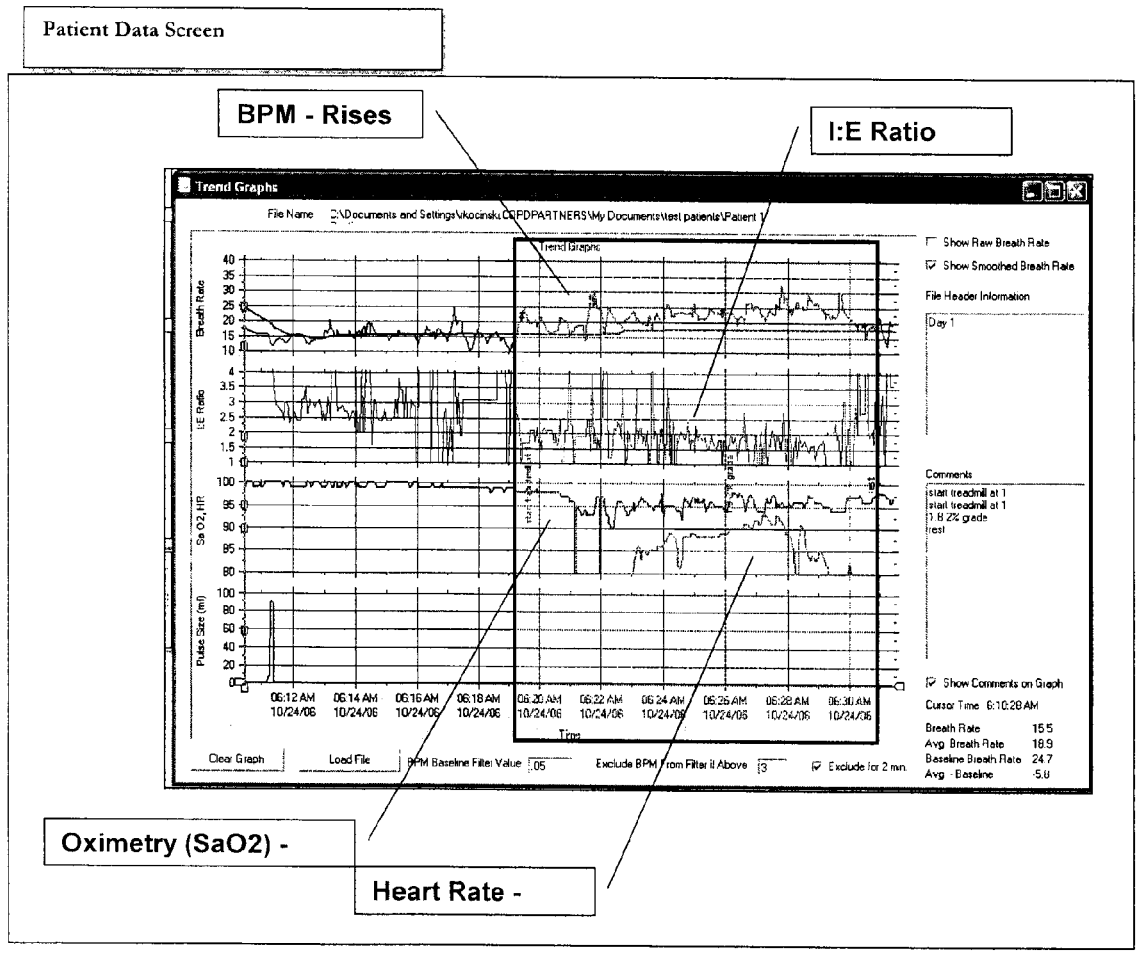
FIG. 3 is a graph of a patient data screen.

A sample output graphic is shown in FIG. 3, and represents an example of one patient who was tested. This was a test of a patient who was on continuous flow oxygen (no doser). The test had the patient rest for 5 minutes, and then exercise on a treadmill for 10 minutes (approximately).

In the Breath Rate graphs in FIG. 3 there are two lines. One is the patient's breath rate (starting below 20 breathes per minute) and the other line is the patient's normal resting breath rate (smooth line staring at 25). The smooth line reflects a smoothed averaged baseline that is derived by taking the Current Breath Rate ($BR_{Cur}$), and the Current Normal Breath Rate ($BR_{CurNorm}$), and weighting them both proportionately, 20%, and 80% respectively, (or some similar ratio), to establish the New Normal Breath Rate ($BR_{NewNorm}$). This calculation is made on every breath.

Figure 5:
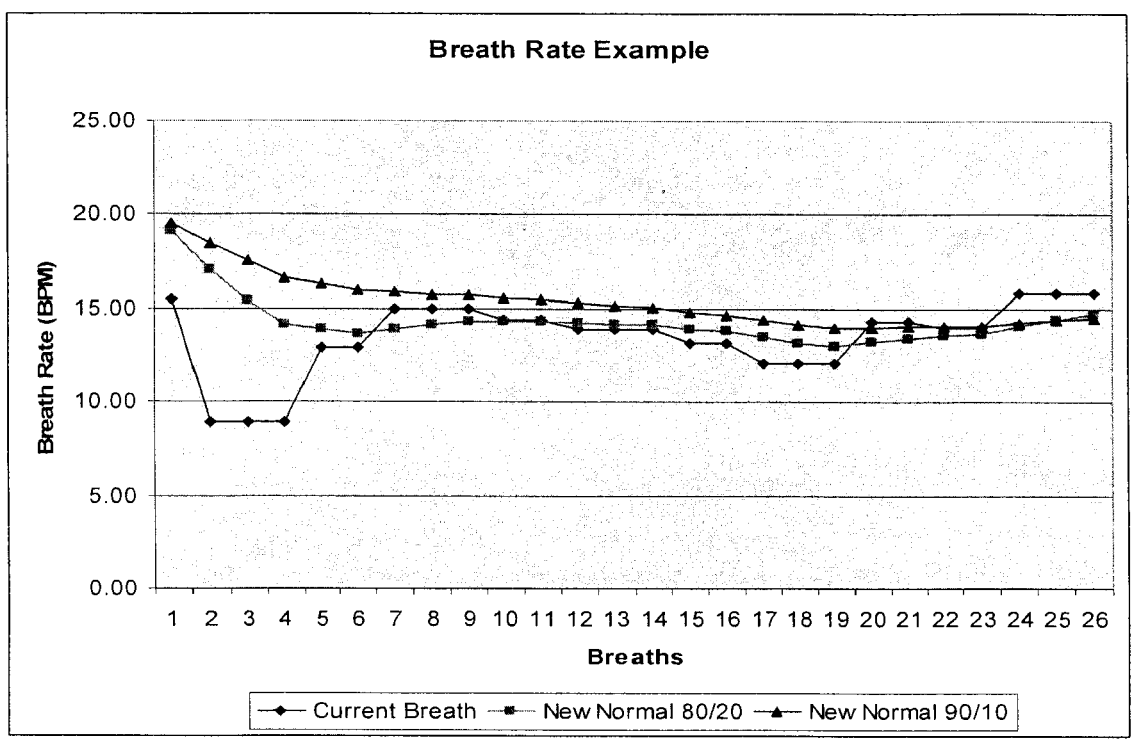
FIG. 5 is a Breath Rate Chart.

Table 1 in FIG. 4 shows an exploded breath-by-breath example of a real patient at start up. We use 20 BPM as the first $BR_{Cur}$ value and then recalculate on each breath. The example is calculated using both an 80/20 smoothing rate, and a 90/10 smoothing rate. This data set is graphed out in FIG. 5. Chart 1 in FIG. 5 shows that the breath rate of a patient can jump around quite a bit, but the smoothed, first order filter breath rate gives a stable baseline that eliminates transients.

As can be seen, the smoothing filter is greater when only 10% weighting is used for the current breath than when a 20% weighting is applied. We have tried values of 5-25% weighting for the current breath rate. The most preferable weighting factor which we are using currently is the 20/80

This smoothing filter allows for patients to be tracked without reacting to short term changes. When a patient begins exercising, their smoothed breath rate could climb as their breath rate goes up. When Sport Mode doses are delivered at +3 and +6 BPM over this baseline, the normal resting breath rate should not move over time with the patient's exertion. In order to hold the normal resting breath rate to a breath rate that indicates rest, breaths from the smoothing calculation while the patient is in Sport Mode are excluded. This means that if a patient's normal resting breath rate is 15 BPM, that when they exceed 18 BPM, an additional dose of oxygen is given, and the breaths are not used in the smoothing filter. Additionally, there is a 2 minute delay after the patient's breath rate crosses back under the Sport Mode threshold (+3) setting before these breathes are used again in the filtering equation. This allows for use of only breaths that are not in Sport Modes (when patient is not at rest) for the calculation of normal resting breath rate and gives a recovery time for a patient who stopped exerting themselves prior to using data for calculation of the normal resting breath rate.

Figure 6:
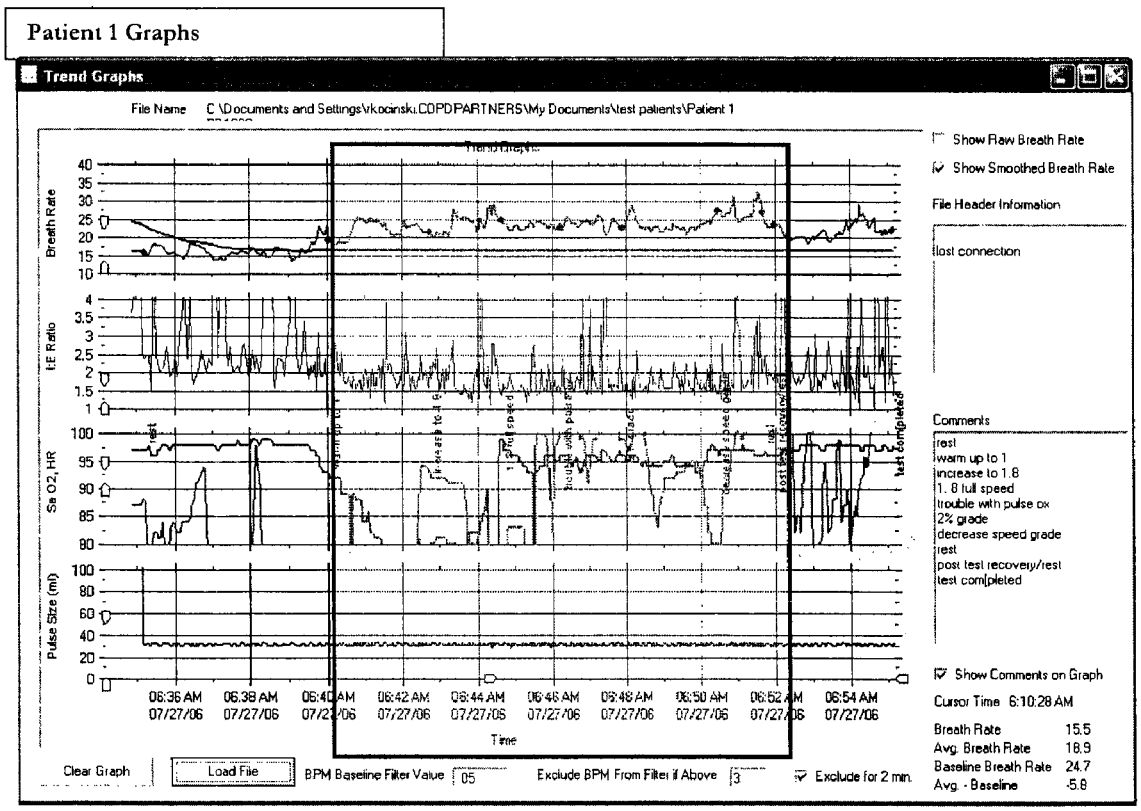
FIG. 6 is a graph of a patient data screen.
Figure 7:
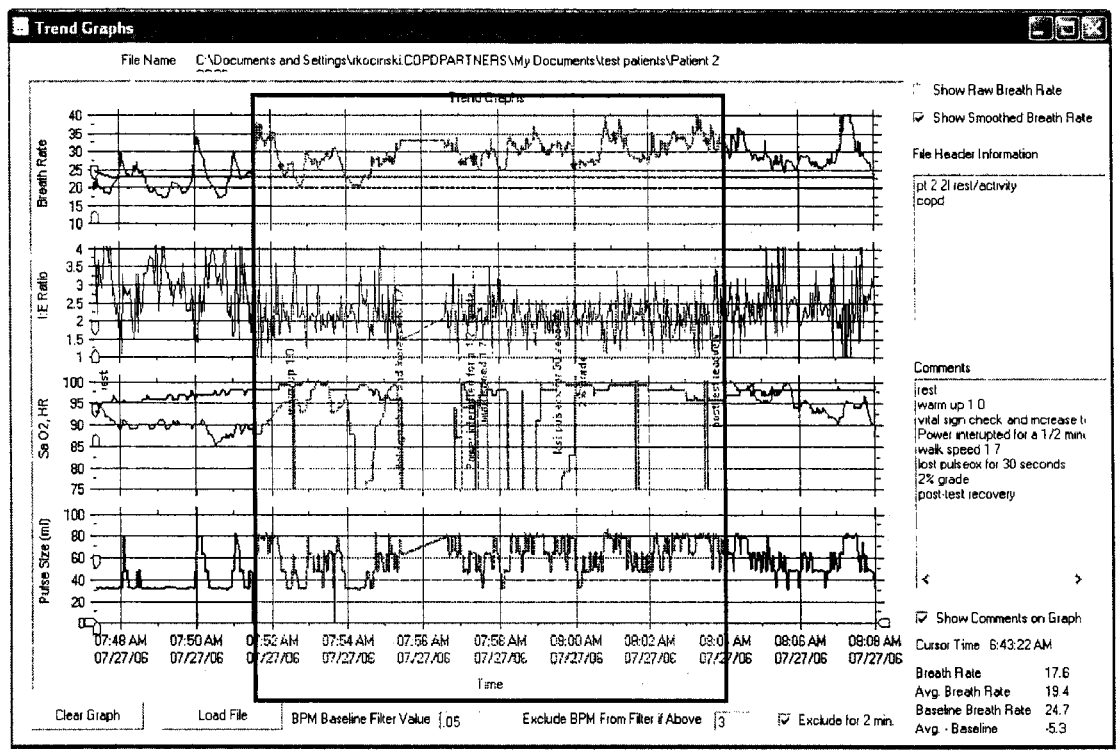
FIG. 7 is a graph of patient data screen.
Figure 8:
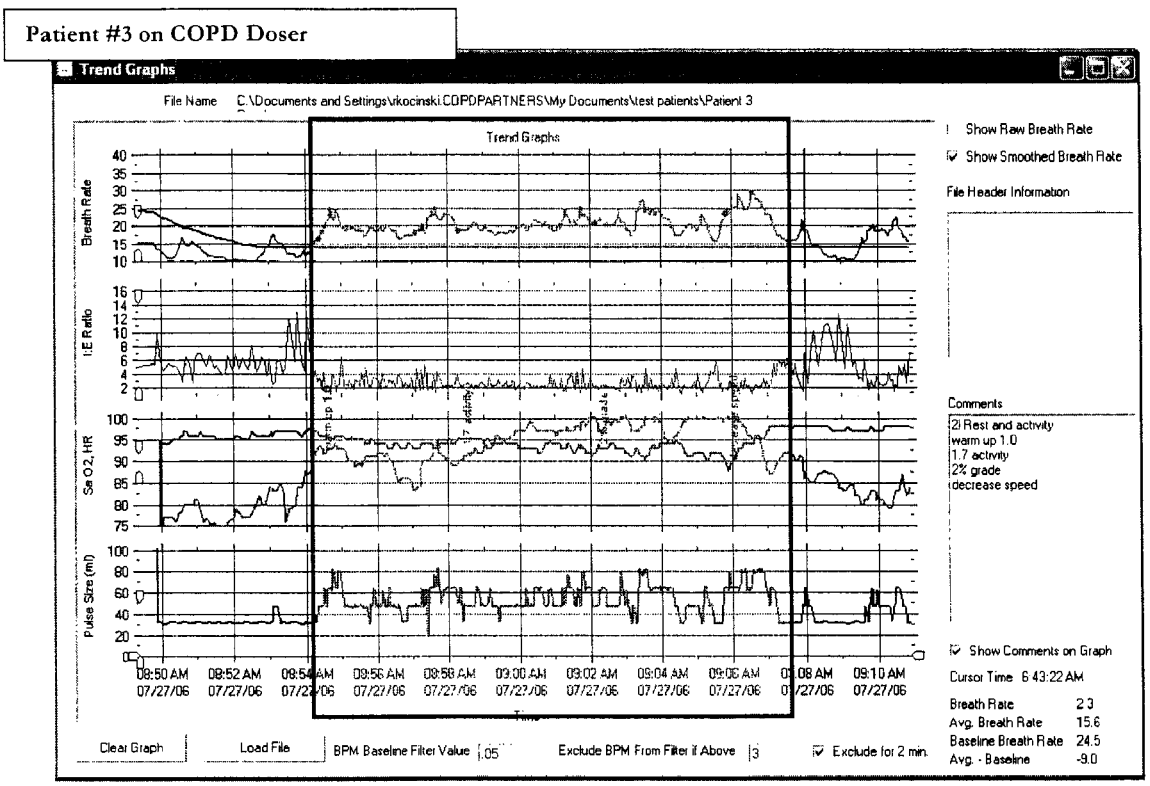
FIG. 8 is a graph of patient data screen.

In order to illustrate the differences between patients, and the need to calculate the normal resting breath rate for each patient, please see FIGS. 6-8.

FIG. 6 shows a patient on a standard conserver that only gives 16 cc per setting (32 cc for a 2 LPM patient). Notice that this patient's resting breath rate is 16 BPM. The shaded area represents exercise. We could see here that using a "Normal Breath Rate" of 20 would not be appropriate for this patient. Notice the desaturation that accompanied exercise by the dip in the top line in the Sa $O_2$, HR row.

FIG. 7 shows another patient whose normal breath rate is more along the lines of 24 BPM. Notice that this patient was on the dosing algorithm, so when they exceeded 3 BPM over their personal threshold, they were given additional oxygen in Sport Modes, 1 & 2. The additional doses are tracked on the bottom graph. We can also see here that the saturation remained stable at >95% Sa $O_2$. Note: The oximeter probe became dislodged during exercise which caused the gaps in reading, but in general could trend to positive results.

FIG. 8 shows yet another patient who underwent the same test protocol and it can clearly be seen that this patient does not have a similar breath rate to the previous examples. The patient in FIG. 8 has a normal resting breath rate of less than 15 BPM. Had the industry norm of 20 BPM been selected as the normal resting breath rate, this patient would not be given additional oxygen when they need it.

The more we monitored patients that were tested, the more it was realized that each patient is different and that re-testing them at later points in time showed additional variances. Patients' conditions change over time and their disease is better and worse on any given day. Because of this, there is not any fixed predetermined value for "normal breath rate" that will work for all patients.

At this time, one embodiment uses two valves in the system, that in combination give a total flow capacity on the order of 13-16 LPM (currently using 14 SLPM flow combination). This flow is selected primarily because this is the maximum flow that most patients can tolerate. The optimum condition is to use the highest flow that the can be used and that is accepted by the patient, because this allows for delivery of the largest dose in the smallest delivery window.

This does not equate to an answer of more valves equals more flow. Other units already give flow in this range with a single valve, and they likewise were selected to be the maximum that the patients can tolerate. The reason for multiple valves (flows) was to be able to NOT deliver maximum flow when it is not needed. If a patient is breathing at a slow rate, sitting, resting, such as in church, they likely do not want or need flows of 16 SLPM to get their dose in the appropriate time.

The higher the flow, the greater the dose that can be delivered in a given delivery window, but the practical limit is patient tolerance. As an example, if 14 SLPM is chosen as the max flow, or an existing unit delivers at 14 SLPM (all the time with one valve/orifice), the dose is equal to:

$$\text{Dose}=\text{Valve on Time}(V_{OT})*\text{Max Flow}(F_{Max})/1000$$

Where:
$V_{OT}$ is in msec
$F_{Max}$ is in ml/sec

If the dose is predetermined and the maximum flow is set, then the only variable is the valve on-time. If the dose is to be delivered within the "delivery window", (60% of the inspiratory cycle), then the patient's inhalation time can not exceed 167% of the valve on-time. This is the practical limit of this device and of every device on the market.

The multiple flows are used to allow the device to stretch the tolerance for short times when more flow is needed while still maintaining lower, acceptable flows when it is not needed. In addition to this, the device gives very low flows when a patient is at rest. As an example, a patient that is on a 2 setting would receive 32 ml dose. Let's assume that they are at rest and breathing at 14 BPM (resting). On a standard doser that delivers at a fixed flow of 14 SLPM, the following would be true:

$$F_{Max}=14 \text{ SLPM}*(1\text{Min}/60 \text{ Sec})*(1000 \text{ ml/Liter})= 233.33 \text{ ml/sec}$$

$$V_{OT}=[(32 \text{ ml})/(233.33 \text{ ml/sec})]*1000=137.14 \text{ msec}$$

This patient's delivery window, assuming an I:E ratio of 1:2, would be:

$$D_{Win}=(60 \text{ sec}/1 \text{ min})*(1 \text{ min}/14 \text{ Breaths})*(\tfrac{1}{3} \text{ Inhale to total breath})*(0.60)=850 \text{ msec}.$$

A fixed flow device operating in this condition, would deliver a dose in 137 msec, when the dose could have been delivered at a much lower flow, up to 850 msec, which is more comfortable for the patient.

This device would have chosen a flow of 4 SLPM, and delivered this dose in:

$$F_{Selected}=4 \text{ SLPM}*(1\text{Min}/60 \text{ Sec})*(1000 \text{ ml/Liter})= 66.67 \text{ ml/sec}$$

$$V_{OT}=[(32 \text{ ml})/(66.67 \text{ ml/sec})]*1000=480 \text{ msec}$$

Note that this is still well within the allowable delivery window, but is at a considerably lower flow and is therefore, very comfortable for the patient, will cause less nasal dryness, and is quieter for the patient. Note that patients are very concerned with the noise that their equipment generates. They would like for their therapy to be as inconspicuous as possible, and lower flow produces lower noise.

In a second embodiment a single proportional valve will be used that will provide a range of flows and therefore allow the device to always use the delivery window to minimize flow. In this same case, the following delivery logic would be used.

$$F_{Selected}=[(32 \text{ ml})/(0.850 \text{ sec})]=37.65 \text{ ml/sec flow}$$

$$(37.65 \text{ ml/sec})*(60 \text{ sec/1Min})*(1 \text{ Liter/1000 ml})=2.26 \text{ SLPM}$$

The first embodiment will allow the device to choose three flows between two valves, A and B, of:

Flow $A$=4 SLPM

Flow $B$=10 SLPM

Flow $A+B$=14 SLPM

With a proportional valve, the device chose the exact flow to allow us to fit the dose into the delivery window.

Figure 2:
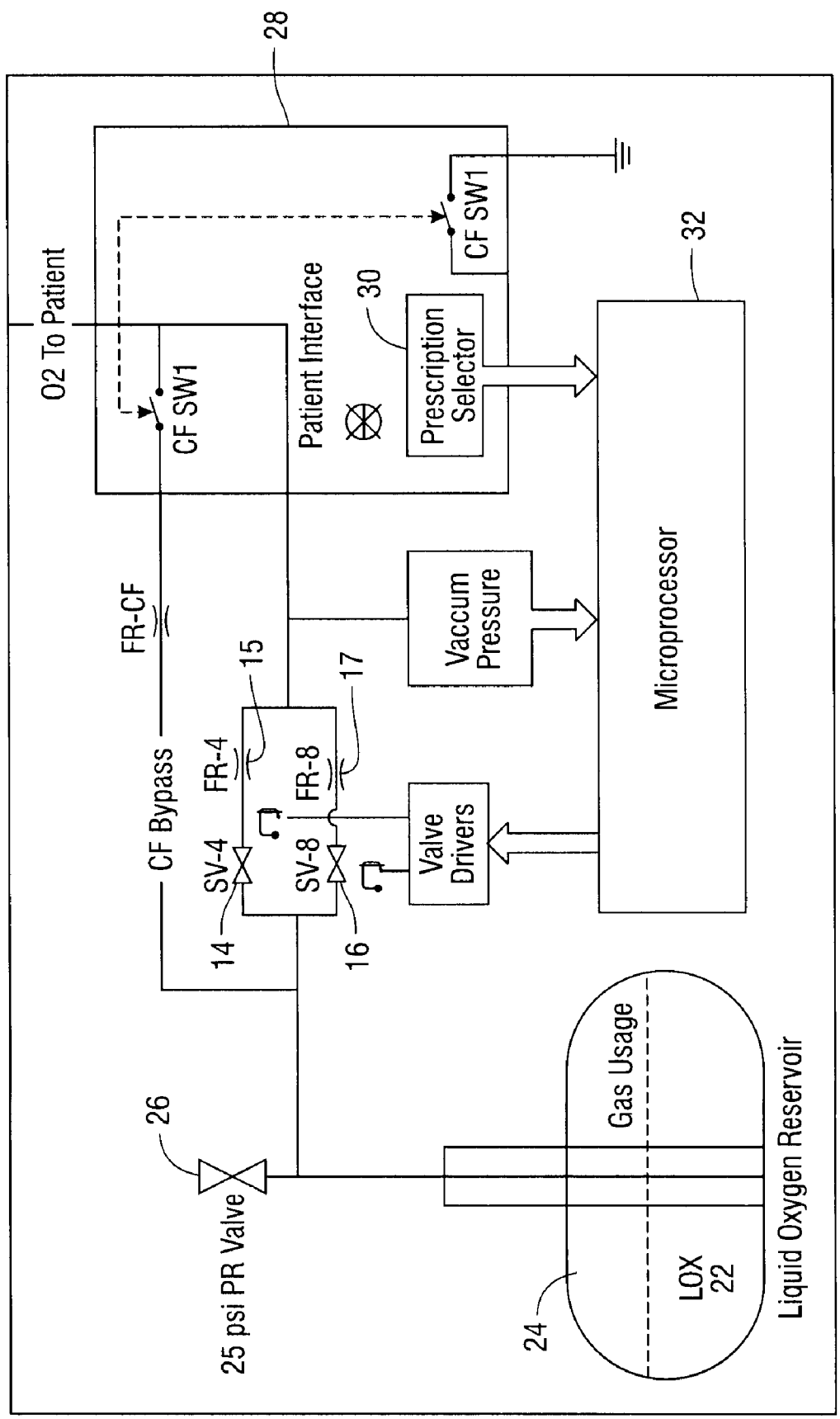
FIG. 2 is a block diagram of the apparatus for providing a dose of a gaseous drug.

With reference to FIG. 2, a therapeutic oxygen gas 22 is supplied from a liquid oxygen Dewar 24. Due to natural heat losses of the container, there is a natural evaporation rate that keeps a gas layer in the Dewar 24 which builds in pressure as more volume converts from liquid to gaseous oxygen. This gas is maintained at a desired pressure of 25 psi by a pressure relief valve 26 embedded in an economizer valve system. The economizer valve system makes use of the gaseous oxygen for patient therapy, and will supplement this with liquid oxygen if needed. When liquid oxygen is used, due to rapid consumption that outpaces the evaporation rate of the Dewar, it is delivered through a length of tubing to warm it to adequate levels prior to delivery to a patient. This system provides oxygen to the dosing system at a static and stable pressure of 25 psig. Note that the dosing system can be altered to various pressures or sources inasmuch as they are at stable pressure.

A patient interface 28 is comprised of a patient selector switch 30 which allows the patient to select their prescribed oxygen flow rate with settings of, 0, 0.5, 1.0, 2.0, 3.0, 4.0, and 5.0 standard liters per minute (SLPM) of oxygen. This selection reflects the continuous flow therapy that the patient was prescribed, and is converted to a breath dose volume by the microprocessor. Base dosing equivalents should preferably reflect 16 cc of oxygen for each SLPM setting such that a flow selection of 1.0 SLPM will result in a base or normal dose of 16 cc, while a flow selection of 2.0 SLPM will result in a base, or normal dose of 32 cc, and so on.

The patient connects to the oxygen port with a cannula tubing, which is internally connected to a pressure sensor 4. The pressure sensor could be a vacuum or pressure sensor 4. When the patient inhales, the pressure sensor 4 output changes. A microprocessor 32 monitors the pressure sensor 4 and converts the analog signal to a digital reading and uses this signal change to indicate transitions between inhalation and exhalation. By monitoring these transitions and tracking with an internal clock, the microprocessor 32 can determine the breath pattern of the patient, specifically, beginning of inhalation, length of inhalation, length of exhalation, length of breath, current breath rate, and the ratio of inhalation to exhalation (I:E ratio). It should be noted that the vacuum/pressure signal should be ignored as a breath indicator during oxygen delivery since the flow out to the patient is carried in the same tube as the vacuum/pressure signal to the sensor. During oxygen delivery, the signal is discarded, or can be used to track that dose was delivered, and then monitored once again after the dose is finished.

As a preferred embodiment, the microprocessor 32 monitors the current breath rate and maintains a filtered normal resting breath rate. It is known that a patients' breath rate increases with exertion, and by excluding higher breath rates from the filtering, a normal resting breath rate can be developed by the microprocessor and is specific to each patient and can change over time. On each breath, the algorithm combines the normal resting breath rate to the current breath, and weights them at 80% and 20% respectively. This then becomes the new normal resting breath rate. Whenever a patient's current breath rate crosses a threshold of >3 breaths per minute (BPM) higher than their normal resting breath rate, it and all subsequent breaths are excluded from this equation, as well as all breaths for an additional 2 minutes. The result is a smoothed normal resting breath rate that reflects a patient's at-rest condition. As an alternative, the unit could also monitor and react to I:E ratio changes as an indicator of rest or exertion. By monitoring the current breath rate, the microprocessor also calculates a delivery window for the next breath that is ⅔ of the inhalation of the current breath.

The apparatus delivers the before mentioned base dose of 16 cc per setting of patient continuous flow setting while the patient is at rest. When the patient's breath rate exceeds 3 BPM over the normal resting breath rate, which is re-calculated on each breath, the microprocessor 32 controls the system to deliver a Sport Mode$_1$ dose that is equivalent to the base dose, plus an additional 16 cc. Additionally, another Sport Mode$_2$ dose, also 16 cc additional, is delivered if the patient exceeds 6 BPM over their normal resting breath rate. In doing so, the apparatus gives a patient more oxygen when they ambulate. In general, the device looks at each breath to monitor if the patient is resting or ambulating, and if they are ambulating, it provides higher doses of oxygen to track their level of exertion.

The apparatus has two solenoid valves 14 and 16 each combined with a flow restrictor 15 and 17 that when opened, allow flows of 4 or 8 SLPM respectively. These two flows (4 & 8 SLPM), along with a 12 SLPM flow when both valves 14 and 16 are opened simultaneously, providing three different flow options for the delivery of the oxygen. While other delivery devices use one flow and only vary the valve on-time to control the dose, this device selects the flow based on the expected delivery window of the next breath in relation to the volume to be delivered. The microprocessor 32 determines the next dose volume as explained previously, and compares this to the delivery window, and then uses the lowest flow option to deliver this volume in the allotted time. The microprocessor 32 then opens one of the two valves 14 or 16, or both 14 and 16 by digital signal to the valve drivers. By maintaining lower flow rates when possible, the patient does not receive excessive flows that push the dose into a very small delivery window that may be appropriate at high breath rates, but is not necessary at lower resting breath rates. By always delivering at the lowest flow option, the device provides a quieter and more subtle oxygen dose delivery when appropriate. This lower flow delivery also minimizes nasal dryness, a common complaint of patients on higher flow dosing systems.

Also included on the patient interface is an LED indicator that is illuminated green during the dose delivery to notify and assure the patient that doses are being delivered, and illuminates red during the dose delivery if the batteries are getting low and alerts them of the need to replace or recharge the batteries.

There is a Continuous Flow/Pulse Delivery (CF/PD) switch on the patient interface that allows a patient to bypass any and all dosing, and to draw oxygen from the source. This is typically considered a backup and is most often used in the event of a low battery condition. In the CF mode, the CF/PD switch routes oxygen through a Flow Restrictor (orifice) such that the continuous flow to the patient is 2 SLPM. This flow restrictor can be changed for other flow rates so that the device can be set up specifically for each patient. This switch routes the flow path, but also engages an electric switch that disables the dosing circuit and prevents the doser from trying to provide pulses while the user has selected continuous flow.

Normal resting breath rate is calculated on every breath except if BRCur is 2 or more breaths per minute greater than BRcurnorm then the normal resting breath rate remains the same and the calculation of does not start again until the BRCu is within 2 of BRcurnorm.

We claim:

1. A method for providing a dose of a gaseous drug to a patient that has a respiratory disorder comprising:
   (a) determining a normal resting breath rate for the patient; with a control circuit including a vacuum sensor, a microprocessor and an internal clock, by:
      (i) sensing transitions between patient inhalations and exhalations,
      (ii) monitoring and tracking the transitions,
      (iii) calculating a current breath rate of the patient,
      (iv) monitoring the current breath rate and determining a filtered normal resting rate specific to the patient by excluding her breath rates, and
      (v) calculating a new normal resting breath rate by combining the current normal resting breath rate and the current breath rate with an algorithm and weighting them respectively to provide a new normal resting breath rate;
   (b) comparing the current breath rate with the normal resting breath rate; and
   (c) providing a dose of the gaseous drug based on the comparison of the current breath rate with the normal breath rate.

2. The method as recited in claim 1 wherein the dose is delivered during a first two-thirds of an inhalation cycle.

3. The method as recited in claim 1 including:
   (a) determining a standard ratio of inhalation time to exhalation time during a breath for a patient;
   (b) monitoring the current ratio of inhalation time to exhalation time;
   (c) comparing the current ratio with the standard ratio; and
   (d) adjusting the dose of the gaseous drug provided based on a change in the ratio of inhalation and exhalation.

4. The method as recited in claim 1 including varying the flow of the dose delivered to the patient so that less flow will be used when the patient is close to normal resting breath rate.

5. The method as recited in claim 1 wherein the dose is provided by the control circuit adjusting a valve to deliver an appropriate dose to the patient.

6. The method as recited in claim 1 wherein the dose is provided by the control circuit choosing from a low flow valve, a high flow valve, or a combination of the low flow and high flow valve to deliver an appropriate dose to the patient.

7. A method for providing a dose of a gaseous drug to a patient that has a respiratory disorder comprising:
   (a) determining a standard ratio of inhalation time to exhalation time during a breath for the patient with a control circuit including a vacuum sensor, a microprocessor and an internal clock,
      (i) sensing transitions between patient inhalations and exhalations,
      (ii) monitoring and tracking the transitions,
      (iii) calculating the current ratio of inhalation time to exhalation time for the patient,
      (iv) monitoring the current ratio of inhalation time to exhalation time and determining a filtered normal standard ratio of inhalation time to exhalation time specific to the patient,
      (v) calculating a new standard ratio of inhalation time to exhalation time by combining the current standard ratio of inhalation time to exhalation time and the current ratio of inhalation time to exhalation time with an algorithm and weighting them respectively to provide a new standard ratio of inhalation time to exhalation time;
   (b) comparing the current ratio of inhalation time to exhalation time with the standard ratio of inhalation time to exhalation time; and
   (c) providing the dose of the gaseous drug based on the comparison of the current ratio of inhalation time to exhalation time with the standard ratio of inhalation time to exhalation time.

8. The method as recited in claim 7 wherein the dose is delivered during a first two-thirds of an inhalation cycle.

9. The method as recited in claim 7 including varying the flow of the dose delivered to the patient so that less flow will be used when the patient is close to the standard ratio of inhalation time to exhalation time.

10. The method as recited in claim 7 wherein the dose is provided by the control circuit adjusting a valve to deliver an appropriate dose to the patient.

11. The method as recited in claim 7 wherein the dose is provided by the control circuit choosing from a low flow valve, a high flow valve, a combination of the low flow and high flow valves or a continuous flow switch to deliver an appropriate dose to the patient.

12. A method for providing a dose of a gaseous drug to a patient that has a respiratory disorder comprising:
   (a) determining a resting inhalation window; for the patient with a control circuit including a vacuum sensor, a microprocessor and an internal clock, by:
      (i) sensing transitions between patient inhalations and exhalations,
      (ii) monitoring and tracking the transitions,
      (iii) calculating a current inhalation window for the patient,
      (iv) monitoring the current inhalation window for the patient and determining a filtered resting inhalation window specific to the patient,
      (v) calculating a new resting inhalation window by combining the current resting inhalation window and the current inhalation window with an algorithm and weighting them respectively to provide the resting inhalation window;
   (b) determining a flow of the dose of the gaseous drug based on a duration of the inhalation window; and
   (c) delivering the dose of the gaseous drug within a second inhalation window at the lowest flow.

13. The method as recited in claim 12 wherein the dose is delivered during a first two-thirds of the second inhalation cycle.

14. The method as recited in claim 12 wherein the dose and flow are provided by the control circuit choosing from a low flow valve, a high flow valve, a combination of the low flow and high flow valves or a continuous flow switch.

15. A dosing apparatus for providing a dose of a gaseous drug to a patient that has a respiratory disorder comprising:
 (a) a control circuit; including a vacuum sensor, a microprocessor, an algorithm, and an internal clock that determines a normal resting breath rate for the patient by:
   (i) sensing transitions between patient inhalations and exhalations,
   (ii) monitoring and tracking the transitions,
   (iii) calculating the current breath rate of the patient,
   (iv) monitoring the current breath rate and determining a filtered normal resting rate specific to the patient by excluding her breath rates, and
   (v) calculating a new normal resting breath rate by combining the current normal resting breath rate and the current breath rate with the algorithm and weighting them respectively to provide a new normal resting breath rate;
 (b) a vacuum pressure sensor that is connected to a patient to sense patient inhalation and transmits the patient inhalation information to the control circuit;
 (c) a connection port for connection to a gaseous drug supply;
 (d) a gaseous drug delivery device that allows the volume of the gaseous drug delivered to the patient to be varied; and
 (e) a power supply that provides power to the apparatus.

16. The apparatus as recited in claim 15 wherein the gaseous drug delivery device comprises:
 (a) a low flow valve controlled by the control circuit; and
 (b) a high flow valve controlled by the control circuit.

17. The apparatus as recited in claim 15 including a continuous flow valve controlled by the control circuit.

18. The apparatus as recited in claim 15 wherein the gaseous drug delivery device comprises a variable flow valve.

19. The apparatus as recited in claim 15 wherein the gaseous drug supply is a liquid oxygen reservoir.

* * * * *